(12) United States Patent
Bombalier

(10) Patent No.: US 8,983,855 B1
(45) Date of Patent: Mar. 17, 2015

(54) SYSTEMS AND METHODS FOR EVALUATING ADHERENCE TO A PROJECT CONTROL PROCESS

(75) Inventor: Ernesto Luis Bombalier, Atlanta, GA (US)

(73) Assignee: McKesson Financial Holdings, Hamilton (BM)

( * ) Notice: Subject to any disclaimer, the term of this patent is extended or adjusted under 35 U.S.C. 154(b) by 425 days.

(21) Appl. No.: 13/108,495

(22) Filed: May 16, 2011

(51) Int. Cl.
　*G06Q 50/00* (2012.01)
　*G06Q 50/22* (2012.01)
　*G06Q 50/24* (2012.01)

(52) U.S. Cl.
　CPC .............. *G06Q 50/22* (2013.01); *G06Q 50/24* (2013.01)
　USPC .................................................. 705/2; 705/3

(58) Field of Classification Search
　CPC ..... G06Q 50/22; G06Q 50/24; G06Q 30/018; G06F 19/30
　USPC .................. 705/2, 3, 7.28; 709/202, 225, 232
　See application file for complete search history.

(56) References Cited

U.S. PATENT DOCUMENTS

| | | | |
|---|---|---|---|
| 5,628,530 A | 5/1997 | Thornton | |
| 5,944,821 A | 8/1999 | Angelo | |
| 6,012,035 A | 1/2000 | Freeman et al. | |
| 6,757,898 B1 | 6/2004 | Ilsen et al. | |
| 6,769,228 B1 | 8/2004 | Mahar | |
| 7,155,397 B2 | 12/2006 | Alexander et al. | |
| 2002/0002495 A1 | 1/2002 | Ullman | |
| 2002/0087583 A1 | 7/2002 | Morgan et al. | |
| 2002/0111832 A1 | 8/2002 | Judge | |
| 2002/0198831 A1 | 12/2002 | Patricelli et al. | |
| 2003/0009367 A1 | 1/2003 | Morrison | |
| 2003/0050799 A1 | 3/2003 | Jay et al. | |
| 2003/0149625 A1 | 8/2003 | Leonardi et al. | |
| 2003/0154163 A1 | 8/2003 | Phillips et al. | |
| 2003/0163488 A1* | 8/2003 | Kloos et al. | 707/200 |
| 2003/0229540 A1 | 12/2003 | Algiene | |
| 2004/0039599 A1 | 2/2004 | Fralic | |
| 2004/0064732 A1 | 4/2004 | Hall | |

(Continued)

FOREIGN PATENT DOCUMENTS

| | | |
|---|---|---|
| CA | 2482370 | 3/2006 |
| WO | 9503569 | 2/1995 |

(Continued)

OTHER PUBLICATIONS

Notice of Allowance for U.S. Appl. No. 13/434,362 mailed Oct. 4, 2013.

(Continued)

*Primary Examiner* — Ricky Ngo
*Assistant Examiner* — Kabir Jahangir
(74) *Attorney, Agent, or Firm* — Sutherland Asbill & Brennan LLP

(57) ABSTRACT

Systems and methods for evaluating adherence to a project control process are provided. A project to be audited may be identified by a computing system comprising one or more computers. The project may be a data delivery project implemented to deliver confidential healthcare information. The results of an audit performed on the identified project may be determined by the computing system. The audit may evaluate adherence of the project to a project control process. Based at least in part upon the results of the audit, the computing system may calculate a process adoption score for the identified project.

18 Claims, 7 Drawing Sheets

(56) References Cited

U.S. PATENT DOCUMENTS

| | | |
|---|---|---|
| 2004/0073457 A1 | 4/2004 | Kalies |
| 2004/0078234 A1 | 4/2004 | Tallal, Jr. |
| 2004/0117323 A1 | 6/2004 | Mindala |
| 2004/0148198 A1 | 7/2004 | Kalies |
| 2004/0249745 A1 | 12/2004 | Baaren |
| 2005/0015280 A1 | 1/2005 | Gabel et al. |
| 2005/0060201 A1 | 3/2005 | Connely et al. |
| 2005/0065824 A1* | 3/2005 | Kohan ............................. 705/3 |
| 2005/0102169 A1 | 5/2005 | Wilson |
| 2005/0102172 A1* | 5/2005 | Sirmans, Jr. ..................... 705/4 |
| 2005/0132205 A1 | 6/2005 | Palliyil et al. |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240473 A1 | 10/2005 | Ayers, Jr. et al. |
| 2005/0251677 A1 | 11/2005 | Maeda et al. |
| 2005/0288972 A1 | 12/2005 | Marvin et al. |
| 2006/0020514 A1 | 1/2006 | Yered |
| 2006/0020821 A1 | 1/2006 | Waltermann et al. |
| 2006/0026041 A1 | 2/2006 | Ullman |
| 2006/0149784 A1 | 7/2006 | Tholl et al. |
| 2006/0184391 A1 | 8/2006 | Barre et al. |
| 2006/0184792 A1 | 8/2006 | Berlin |
| 2006/0259363 A1 | 11/2006 | Jhetam et al. |
| 2007/0005402 A1 | 1/2007 | Kennedy et al. |
| 2007/0050209 A1 | 3/2007 | Yered |
| 2007/0061596 A1 | 3/2007 | Ferguson et al. |
| 2007/0118729 A1 | 5/2007 | Adams et al. |
| 2007/0136100 A1 | 6/2007 | Daugherty et al. |
| 2007/0150314 A1* | 6/2007 | Abraham-Fuchs et al. ....... 705/3 |
| 2007/0203768 A1* | 8/2007 | Adra ............................... 705/7 |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2008/0134297 A1 | 6/2008 | Clinick et al. |
| 2009/0031141 A1 | 1/2009 | Pearson et al. |
| 2009/0112643 A1* | 4/2009 | Brys et al. ........................ 705/7 |
| 2010/0094836 A1* | 4/2010 | Duncan et al. ................ 707/705 |
| 2010/0100963 A1 | 4/2010 | Mahaffey |
| 2010/0225447 A1* | 9/2010 | Adra ............................ 340/10.1 |
| 2010/0293388 A1 | 11/2010 | Ammer et al. |
| 2011/0055041 A1* | 3/2011 | Shaw et al. ................... 705/26.3 |
| 2011/0154028 A1 | 6/2011 | Kirkup et al. |
| 2011/0185417 A1 | 7/2011 | Zhou et al. |
| 2011/0191145 A1* | 8/2011 | Ford et al. ..................... 705/7.38 |
| 2011/0225655 A1 | 9/2011 | Niemel et al. |
| 2012/0004945 A1* | 1/2012 | Vaswani ...................... 705/7.28 |
| 2012/0072725 A1 | 3/2012 | Fanton et al. |
| 2012/0116984 A1* | 5/2012 | Hoang et al. .................. 705/317 |
| 2012/0166353 A1* | 6/2012 | Evanitsky ...................... 705/342 |
| 2012/0198514 A1 | 8/2012 | McCune et al. |
| 2013/0145472 A1 | 6/2013 | Ramabhatta et al. |

FOREIGN PATENT DOCUMENTS

| | | |
|---|---|---|
| WO | 0039737 | 7/2000 |
| WO | 2007025295 | 3/2007 |

OTHER PUBLICATIONS

Sampson, R.J., Taking Control of Health Care Costs, Best's Review—Life Health Insurance Edition, Nov. 1983, vol. 84, Issue 7, USA; Abstract only.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, vol. 63, Issue 1, USA; Abstract only.

Anonymous, TechRx Announces Successful Beta Deployment of T-Rex. PR Newswire. May 13, 2002.

Non-Final Office Action for U.S. Appl. No. 13/434,362 mailed Jul. 22, 2013.

* cited by examiner

SYSTEMS AND METHODS FOR EVALUATING ADHERENCE TO A PROJECT CONTROL PROCESS

FIELD OF THE INVENTION

Aspects of the invention relate generally to the delivery of confidential healthcare information, and more particularly, to systems and methods for evaluating projects to deliver confidential healthcare information to assess adherence of the projects to a project control process.

BACKGROUND OF THE INVENTION

A wide variety of healthcare transactions, such as prescription claim transactions, are typically processed and/or routed through a service provider. For example, claim transactions are typically received by the service provider from healthcare providers (e.g., pharmacies) and routed to payers. Similarly, adjudicated responses to claim transactions are typically received by the service provider from the payers and routed to the healthcare providers. During the processing and routing of healthcare transactions, a wide variety of healthcare information may be stored by the service provider. The stored data, along with a wide variety of other healthcare data, may subsequently be accessed by the service provider and utilized to generate or prepare data deliverables that are provided to customers of the service provider. For example, various reports associated with processed healthcare transactions may be provided to a healthcare provider.

In many instances, the information that is included in a data deliverable includes confidential and/or proprietary healthcare information. In order to protect the security of this information, control processes for preparing the data deliverables have been developed. These processes include various steps and procedures that should be followed in order to mitigate risk associated with the data deliverables. However, these processes are only useful if they are adhered to and followed. Accordingly, there is an opportunity for systems and methods for evaluating adherence to project control processes.

BRIEF DESCRIPTION OF THE INVENTION

Some or all of the above needs and/or problems may be addressed by certain embodiments of the invention. Embodiments of the invention may include systems and methods for evaluating adherence to a project control process. In one embodiment, a method for evaluating adherence may be provided. A project to be audited may be identified by a computing system comprising one or more computers. The project may be a data delivery project implemented to deliver confidential healthcare information. The results of an audit performed on the identified project may be determined by the computing system. The audit may evaluate adherence of the project to a project control process. Based at least in part upon the results of the audit, the computing system may calculate a process adoption score for the identified project.

In accordance with another embodiment of the invention, a system may be provided. The system may include at least one memory and at least one processor. The at least one memory may be operable to store computer-executable instructions. The at least one processor may be configured to access the at least one memory and execute the computer-executable instructions to: identify a project to be audited, the project, comprising a data delivery project implemented to deliver confidential healthcare information; determine the results of an audit performed on the identified project, wherein the audit evaluates adherence of the project to a project control process; and calculate, based at least in part upon the results of the audit, a process adoption score for the identified project.

Additional systems, methods, apparatus, features, and aspects may be realized through the techniques of various embodiments of the invention. Other embodiments and aspects of the invention are described in detail herein with reference to the description and to the drawings and are considered a part of the claimed invention.

BRIEF DESCRIPTION OF THE DRAWINGS

Reference will now be made to the accompanying drawings, which are not necessarily drawn to scale, and wherein.

DETAILED DESCRIPTION OF THE INVENTION

Figure 1:
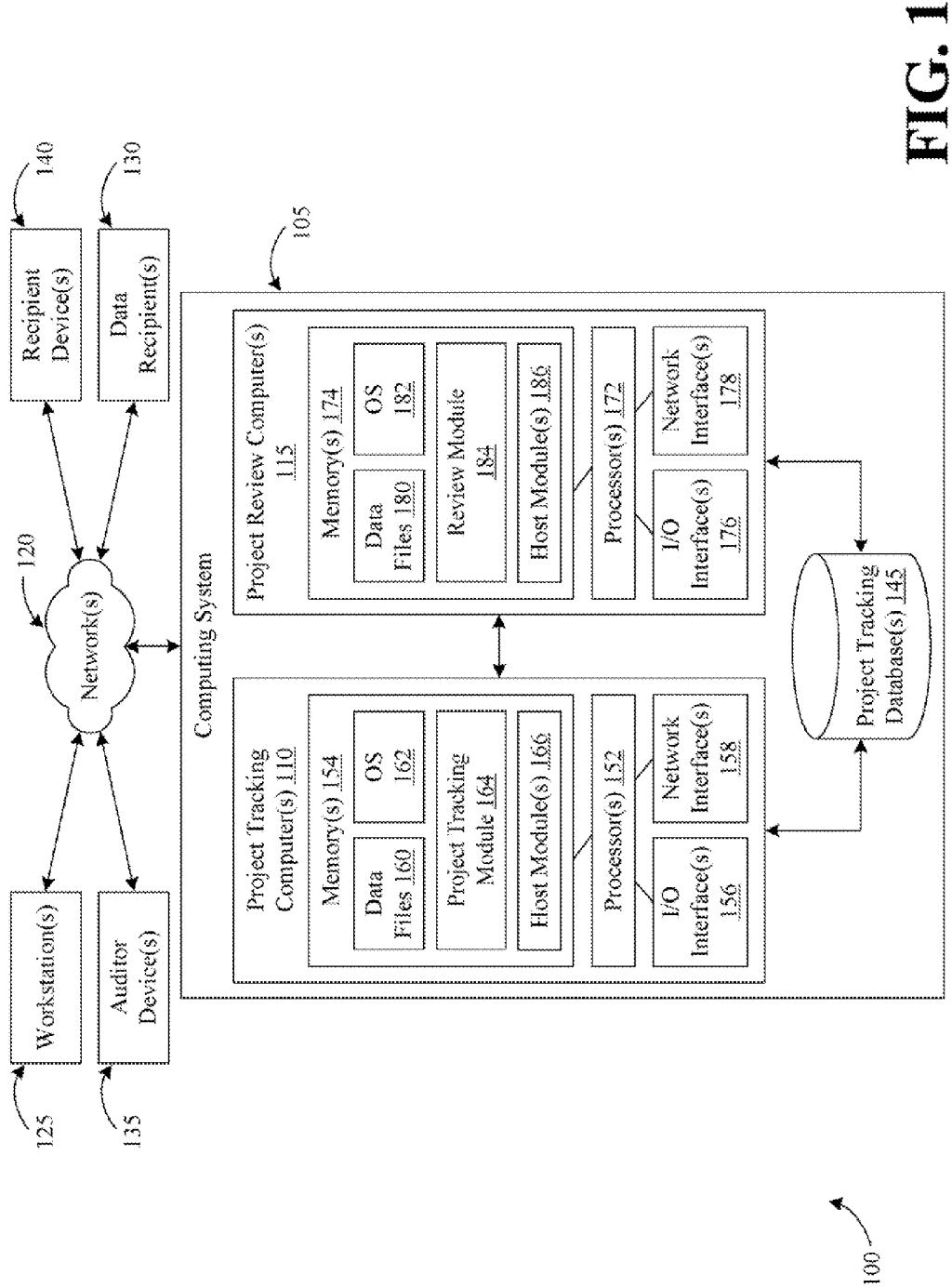
FIG. 1 illustrates an example overview of a system that may facilitate the evaluation of project adherence to a project control process, according to an example embodiment of the invention.

Embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments of the invention may include systems, methods, and apparatus for evaluating the adherence of data delivery projects to a project control process. In certain embodiments, one or more processes may be put in place to control the development of data delivery projects. A wide variety of different types of data delivery projects may be subject to a project control process, such as one time or ad-hoc queries of healthcare information (e.g., healthcare claim transactions, eligibility requests, etc.) and/or data feeds established to deliver healthcare information in a recurring manner. A project control process may include any number of guidelines and/or project checkpoints. During the completion of a data delivery project, a project developer, programmer, or technician may be instructed to follow the project control process. Various steps performed by the developer may be tracked by a suitable project tracking system. For example, information associated with process checkpoints may be tracked.

Following the completion of one or more projects, at least one project may be identified and/or selected for auditing purposes. A wide variety of suitable methods and/or techniques may be utilized to identify a project for audit. For example, in certain embodiments, a project may be identified based at least in part upon the receipt of a project selection from an auditor. In certain embodiments, a list of projects that are available for audit may be presented to an auditor, and a project selection may be received. As another example, tracking information for completed projects may be evaluated utilizing one or more suitable identification parameters, and a project may be selected for an audit based at least in part upon the evaluation. For example, a project having unexpected dates for one or more benchmarks and/or any number of other identifiable criteria that do not satisfy expected values may be identified. Additionally, as desired in certain embodiments, one or more projects may be periodically identified for audit purposes. For example, a fixed number of projects may be identified in a month. In other embodiments, projects may be automatically audited following completion.

Once a project has been identified for an audit, an audit may be performed on the project, and the results of the audit may be identified. The audit may evaluate adherence of the project to a project control process. In other words, the audit may evaluate whether the project control process has been properly utilized during the development of the project. In this regard, a determination may be made as to whether the process is being adopted and/or followed. A wide variety of suitable methods and/or techniques may be utilized as desired to identify the results of an audit. In certain embodiments, one or more audit forms may be provided to an auditor along with project tracking information, and the auditor may perform a manual audit of the project. The results of the manual audit may then be returned to a suitable computing system that identifies and further processes the results. In other embodiments, an audit may be performed in an automated fashion. For example, one or more audit parameters and/or checkpoints may be identified, and project tracking information may be evaluated utilizing the parameters and/or checkpoints.

In certain embodiments, an audit may determine whether various steps or checkpoints associated with a project control process have been adhered to and/or followed. Additionally, as desired, an audit may determine whether the completion of various steps of the process have been properly documented. In certain embodiments, an audit may be an objective audit in which respective values are assigned to each of the checkpoints and/or documentation parameters. As desired, the respective values assigned to each of the checkpoints and/or parameters may be weighted based upon the respective importance of the checkpoints (e.g., the security risk if the checkpoint is not completed or followed, etc.). Once the audit results have been determined, the results may be evaluated in order to calculate a process adoption score for the project. For example, the respective values for each of the checkpoints may be summed together in order to calculate a process adoption score. The process adoption score may be indicative of the adherence of the project development or generation to the project control process. Additionally, the results may be evaluated in order to determine whether any exceptions are present (e.g., an exception associated with a checkpoint not being achieved, etc.). As desired, any number of control actions may be taken based upon identified exceptions and/or the calculated project adoption score. For example, alert messages may be communicated to a supervisor of a technician who completed the project. In this regard, corrective action may be taken to promote adoption of the project control process.

System Overview

An example system 100 that facilitates the evaluation of project adherence to a project control process will now be described illustratively with respect to FIG. 1. As shown in FIG. 1, the system 100 may include at least one computing system 105 that facilitates project management and/or project review. In certain embodiments, the computing system 105 may include one or more project tracking computers 110 and/or one or more project review computers 115. Additionally, the computing system 105 may be in communication with any number of other devices and/or systems via one or more suitable networks 120. For example, the computing system 105 may be in communication with one or more workstations 125, one or more data recipients 130, one or more auditor devices 135, and/or one or more recipient devices 140. As desired, each of the computing system 105, workstations 125, data recipients 130, auditor devices 135, and/or recipient devices 140 may include one or more processing devices that may be configured for accessing and reading associated computer-readable media having stored thereon data and/or computer-executable instructions for implementing the various methods of the invention.

In one example implementation of the system 100, a technician or other individual may utilize a workstation 125 to generate or develop a data delivery project, such as an ad-hoc query of healthcare information or a recurring data feed. During the development of the project, the project may be tracked, and the project tracking computers 110 may store project tracking information in one or more suitable project tracking databases 145. Once the project has been completed, a data deliverable may be communicated to a data recipient 130, such as a healthcare provider system (e.g., a pharmacy computer, a pharmacy chain computer, a hospital computer, etc.). Additionally, the project review computers 115 may identify the completed project as a project to be audited for adherence to a project control process. In certain embodiments, the project review computers 115 may utilize stored project tracking data to complete an audit of the project. In other embodiments, the project review computers 115 may provide project tracking information and/or an audit form to an auditor device 135, and an auditor utilizing the auditor device 135 may complete an audit or review of the project. The auditor device 135 may then provide audit results to the project review computers 115. Once audit results are determined and/or identified, the project review computers 115 may calculate a process adoption score for the project and, as desired, identify exceptions and/or alerts associated with the audit results and/or the process adoption score. Audit information and/or various alerts may then be provided by the project review computers 115 to the recipient devices 140.

Generally, network devices and systems, including one or more of the computing system 105, the workstations 125, the data recipients 130, the auditor devices 135, and/or the recipient devices 140 may include or otherwise be associated with suitable hardware and/or software for transmitting and receiving data, signals, and/or computer-executable instructions over one or more communications links or networks. As desired, these network devices and systems may also include any number of processors for processing data and executing computer-executable instructions, as well as other internal and peripheral components that are well-known in the art. Further, these network devices and systems may include or may be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the computing system 105, the workstations 125, the data recipients 130, the auditor devices 135, and/or the recipient devices 140 may be in communication with each other via one or more networks, such as networks 120, which as described below can include one or more separate or shared private and public networks, including the Internet and/or a publicly switched telephone network. Each of these components—the computing system 105, the workstations 125, the data recipients 130, the auditor devices 135, and/or the recipient devices 140—will now be discussed in further detail.

The computing system 105 may include any number of suitable computing and/or processing devices. Additionally, in certain embodiments, the computing system 105 may be associated with a suitable service provider that processes healthcare information. For example, the computing system 105 may be associated with a suitable healthcare switching service provider that processes and routes healthcare transactions (e.g., prescription claim transactions, Medicare transactions, eligibility requests, prescription requests, etc.) between various healthcare systems, such as healthcare provider computers (e.g., pharmacy computers, hospital computers, physician computers, etc.) and third party processors (e.g., claims processors, prescription benefits managers, etc.). As such, the computing system 105 may be configured to collect and/or store a wide variety of healthcare information. The collected information may be utilized as desired to generate a wide variety of different types of data deliverables, such as ad-hoc queries and/or data feeds prepared on behalf of customers of the computing system 105 (e.g., healthcare providers, third party processors, etc.). For purposes of this disclosure, the preparation of a data deliverable will be referred to as a project. Additionally, to provide security for confidential healthcare information, one or more project control processes may be implemented by the service provider to govern the preparation and/or completion of a project.

With continued reference to FIG. 1, any number of project tracking computers 110 may be provided. A project tracking computer 110 may be any suitable processor-driven device that facilitates the tracking of data delivery projects and/or the storage of tracking information associated with the data delivery projects. For example, the project tracking computer 110 may be a server computer, a mainframe computer, one or more networked computers, a desktop computer, a personal computer, a digital assistant, a personal digital assistant, a digital tablet, an Internet appliance, an application-specific circuit, a microcontroller, a minicomputer, or any other processor-based device. The execution of computer-implemented instructions by the project tracking computer 110 may form a special purpose computer or other particular machine operable to facilitate the tracking of data delivery projects and/or the storage of tracking information associated with the projects. Additionally, in certain embodiments of the invention, the operations and/or control of the project tracking computer 110 may be distributed among several processing components.

In addition to having one or more processors 152, the project tracking computer 110 may include one or more memory devices 154, one or more input/output ("I/O") interface(s) 156, and/or one or more network interface(s) 158. The memory devices 154 may be any suitable memory devices, for example, caches, read-only memory devices, random access memory devices, magnetic storage devices, removable storage devices, etc. The memory devices 154 may store data, executable instructions, and/or various program modules utilized by the project tracking computer 110, for example, data files 160, an operating system ("OS") 162, a project tracking module 164, and/or one or more host modules 166. The data files 160 may include any suitable data that facilitates the receipt of project information, the tracking of projects, and/or the storage and/or access of project tracking information. For example, the data files 160 may include, but are not limited to, control process checkpoints and/or parameters associated with project development, implementation, documentation, and/or completion, forms and/or interfaces that facilitate the entry of project tracking information, and/or received project tracking information. The OS 162 may be a suitable software module that controls the general operation of the project tracking computer 110. The OS 162 may also facilitate the execution of other software modules by the one or more processors 152, for example, the project tracking module 164 and/or the host modules 166. The OS 162 may be, but is not limited to, Microsoft Windows®, Apple OSX™, Linux, Unix, or a mainframe operating system.

Each host module 166 may be a suitable program or processing module, such as a Web server module, that facilitates the hosting of communications sessions with other components of the system 100. For example, a host module 166 may facilitate the establishment of a communications session with a workstation 125 in order to receive project tracking information associated with a project. As another example, a host module 166 may facilitate the establishment of a communications session with an auditor device 135 in order to provide project tracking information to the auditor device 135 in association with an audit that is being completed.

The project tracking module 164 may be a suitable software module or application that facilitates the storage and/or management of project tracking information. In operation, the project tracking module 164 may receive information associated with a project from one or more workstations 125, and the project tracking module 164 may direct the storage of tracking information in one or more suitable project tracking databases 145. A wide variety of tracking information may be stored as desired in various embodiments, of the invention, such as information associated with a plurality of steps or checkpoints associated with the completion of a project and/or a project control process. As desired, any number of checkpoints may be associated with a project control process. One example project control process is described in greater detail below with reference to FIG. 3; however, it will be appreciated that other processes may be utilized as desired.

In certain embodiments, the project tracking module 164 may additionally control the management of a project. For example, the project tracking module 164 may provide directions and/or checkpoint information to the one or more workstations 125 during the development of the project. In certain embodiments, a suitable Web application may be utilized to provide directions to a workstation 125. Additionally, during the development and/or completion of the project, the project tracking module 164 may store project documentation, notes, critical date information, and/or other project tracking information in the databases 145. For example, in certain embodiments, the project tracking module 164 may manage the various checkpoints and store information as the checkpoints are achieved. In this regard, information that permits a subsequent audit of the project may be stored. In one example embodiment, the project tracking module 164 may utilize a version of JTrac, which is an open source issue-tracking Web application that facilitates the collection of project tracking information.

Additionally, in certain embodiments, the project tracking module 164 may be configured to provide stored project tracking information to one or more other components of the system 100, such as the project review computers 115 and/or an auditor device 135. For example, during the completion of an audit, an auditor may utilize an auditor device 135 to access a host module 166 associated with the project tracking computer 110. During a communications session established between the auditor device 135 and the project tracking computer 110, the project tracking module 164 may provide project tracking information that may be utilized by an auditor to complete a project audit. As another example, the project tracking module 164 may provide project tracking information to the project review computers 115. The project review computers 115 may then either process the tracking information to conduct an audit or provide the tracking information to an auditor device 135.

With continued reference to the project tracking computer 110, the one or more I/O interfaces 156 may facilitate communication between the project tracking computer 110 and one or more input/output devices, for example, one or more user interface devices, such as a display, keypad, control panel, touch screen display, remote control, microphone, etc., that facilitate user interaction with the project tracking computer 110. The one or more network interfaces 158 may facilitate connection of the project tracking computer 110 to one or more suitable networks, for example, the networks 120 illustrated in FIG. 1. In this regard, the project tracking computer 110 may receive and/or communicate information to other network components of the system 100, such as the workstations 125 and/or the auditor devices 135.

With continued reference to FIG. 1, any number of project review computers 115 may be provided. A project review computer 115 may be any suitable processor-driven device that facilitates the identification of projects to be audited and the calculation of process adoption scores indicative of the adherence of projects to various project control processes. For example, the project review computer 115 may be a server computer, a mainframe computer, one or more networked computers, a desktop computer, a personal computer, a digital assistant, a personal digital assistant, a digital tablet, an Internet appliance, an application-specific circuit, a microcontroller, a minicomputer, or any other processor-based device. The execution of computer-implemented instructions by the project review computer 115 may form a special purpose computer or other particular machine operable to facilitate the identification of a project to be audited or reviewed, the audit of a project, the review of audit results, and/or the calculation of a process adoption score. In this regard, the project review computer 115 may determine whether a project control process is being implemented, adopted, adhered to, and/or followed during the generation and/or completion of a project. Additionally, in certain embodiments of the invention, the operations and/or control of the project review computer 115 may be distributed among several processing components.

In addition to having one or more processors 172, the project review computer 115 may include one or more memory devices 174, one or more input/output ("I/O") interface(s) 176, and/or one or more network interface(s) 178. The memory devices 174 may be any suitable memory devices, for example, caches, read-only memory devices, random access memory devices, magnetic storage devices, removable storage devices, etc. The memory devices 174 may store data, executable instructions, and/or various program modules utilized by the project review computer 115, for example, data files 180, an operating system ("OS") 182, a review module 184, and/or one or more host modules 186. The data files 180 may include any suitable data that facilitates the identification of one or more projects to audit, the completion of an audit, the review of audit results, the calculation of a process adoption score, and/or the generation of one or more messages and/or alerts associated with audits and/or process adoption scores. For example, the data files 180 may include, but are not limited to, identification information for completed projects, parameters for identifying projects to be audited, checkpoint information and/or audit parameters, audit form information, rules and/or algorithms for conducting audits, audit result information, parameters and/or algorithms for calculating a process adoption score, process adoption score information, parameters for identifying exceptions and/or generating alerts, and/or generated messages. The OS 182 may be a suitable software module that controls the general operation of the project review computer 115. The OS 182 may also facilitate the execution of other software modules by the one or more processors 172, for example, the review module 184 and/or the host modules 186. The OS 182 may be, but is not limited to, Microsoft Windows®, Apple OSX™, Linux, Unix, or a mainframe operating system.

Each host module 186 may be a suitable program or processing module, such as a Web server module, that facilitates the hosting of communications sessions with other components of the system 100. For example, a host module 186 may facilitate the establishment of a communications session with an auditor device 135 in order to provide audit forms and/or project tracking information to the auditor device 135 and/or to review audit results from the auditor device 135. As another example, a host module 186 may facilitate the establishment of a communications session with an auditor device 135 in order to provide a list of projects available to be audited to the auditor device 135 and to receive a selection of a project to be audited.

The review module 184 may be a suitable software module or application that facilitates the identification of a project to be audited, the generation and/or review of audit results, the calculation of a process adoption score, and/or the generation of one or more messages associated with the audit results and/or process adoption score. In one example operation, the review module 184 may identify and/or select a project to be audited. A wide variety of suitable methods and/or techniques may be utilized to identify a project for audit. For example, in certain embodiments, the review module 184 may generate a list of completed projects that are available for audit, and the list may be provided to an auditor device 135 for presentation to an auditor. A selection of a project for audit may then be received from the auditor device 135. As desired, completed projects may be sorted in a wide variety of different ways (e.g., random sorting) prior to presenting a list to an auditor. The sorting may be completed, for example, by the review module 184, by the auditor device 135, or based upon the receipt of auditor instructions.

As another example of identifying a project to be audited, tracking information for completed projects may be evaluated by the review module 184. For example, one or more suitable project identification parameters may be utilized to evaluate stored tracking information, and a project may be selected for an audit based at least in part upon the evaluation. A wide variety of different identification parameters may be utilized as desired, such as date parameters, notes field parameters, and/or project documentation parameters. Additionally, a wide variety of different evaluations may be made utilizing the identification parameters. As one example, a project having unexpected dates for one or more benchmarks and/or any number of other identifiable criteria that do not satisfy expected values may be identified by the review module 184 as a project to be audited. Additionally, as desired in certain embodiments, one or more projects may be periodically identified by the review module 184 for audit purposes. For example, a fixed number of projects may be identified in a month. In other embodiments, projects may be automatically identified for audits by the review module 184 during their development or following completion.

Once a project has been identified for an audit, an audit may be performed on the project, and the results of the audit may be identified by the review module 184. The audit may evaluate adherence of the project to a project control process. In other words, the audit may evaluate whether the project control process has been properly utilized during the development of the project. In this regard, a determination may be made as to whether the process is being adopted and/or followed. A wide variety of suitable methods and/or techniques may be utilized as desired to identify the results of an audit. In certain embodiments, the review module 184 may generate and/or access one or more audit forms associated with the project, and the forms may be provided to an auditor device 135 for manual audit completion. In certain embodiments, the review module 184 may additionally provide project tracking information to the auditor device 135 for review during an audit. Alternatively, the project tracking computers 110 may provide project tracking information to the auditor device 135. Once an audit has been performed, the results of the audit may be received from the auditor device 135 and processed by the review module 184.

In other embodiments, an audit may be performed for the project in an automated fashion. For example, the review module 184 may identify and/or determine one or more audit parameters and/or checkpoints for an audit. A wide variety of checkpoints and/or parameters may be utilized as desired in various embodiments of the invention, such as checkpoints and/or parameters associated with the proper completion of different steps included in a project control process and/or the proper documentation of the various steps. Once the checkpoints and/or parameters have been identified, the review module 184 may utilize the checkpoints and/or parameters to evaluate and/or analyze project tracking information for the project. For example, the review module 184 may evaluate the project tracking information in order to determine whether each step (or checkpoint) in the project control process has been followed and/or whether the completion of the steps has been properly documented by a technician who developed the project.

According to an aspect of the invention, an audit may determine whether various steps or checkpoints associated with a project control process have been adhered to and/or followed. Additionally, as desired, an audit may determine whether the completion of various steps of the process has been properly documented. In certain embodiments, an audit may be an objective audit in which respective values are assigned to each of the checkpoints and/or documentation parameters. As desired, the respective values assigned to each of the checkpoints and/or parameters may be weighted based upon the respective importance of the checkpoints (e.g., the security risk if the checkpoint is not completed or followed, etc.). Once the audit results have been determined, the results may be evaluated by the review module 184 in order to calculate a process adoption score for the project. For example, the respective values for each of the checkpoints may be summed together in order to calculate a process adoption score. The process adoption score may be indicative of the adherence of the project development or generation to the project control process. Additionally, the results may be evaluated by the review module 184 in order to determine whether any exceptions are present (e.g., an exception associated with a checkpoint not being achieved, etc.). As desired, any number of control actions may be taken by the review module 184 based upon identified exceptions and/or the calculated project adoption score. For example, alert messages may be communicated to a recipient device 140 associated with a supervisor of a technician who completed the project. In this regard, corrective action may be taken to promote adoption of the project control process.

One example of the operations that may be performed by the review module 184 is described in greater detail below with reference to FIGS. 4-6.

With continued reference to the project review computer 115, the one or more I/O interfaces 176 may facilitate communication between the project review computer 115 and one or more input/output devices, for example, one or more user interface devices, such as a display, keypad, control panel, touch screen display, remote control, microphone, etc., that facilitate user interaction with the project review computer 115. The one or more network interfaces 178 may facilitate connection of the project review computer 115 to one or more suitable networks, for example, the networks 120 illustrated in FIG. 1. In this regard, the project review computer 115 may receive and/or communicate information to other network components of the system 100, such as the auditor devices 135.

Although the project tracking computers 110 and the project review computers 115 are described as separate devices, in certain embodiments, one or more operations of the project tracking computers 110 and the project review computers 115 may be performed by a single computing device. Alternatively, the operations described for the project tracking computers 110 and the project review computers 115 may be distributed among additional computing systems.

With continued reference to FIG. 1, any number of workstations 125 may be provided. Each workstation 125 may be a suitable processor-driven device that facilitates the development of data delivery projects. As such, a workstation 125 may include components similar to those described above for the project tracking computers 110 and/or the project review computers 115. For example, a workstation 125 may include any number of processors, memory devices, I/O interfaces, and/or network interfaces. In operation, a technician may utilize a workstation 125 to generate or produce a data delivery project. For example, the workstation 125 may be utilized to access stored healthcare information and prepare a data deliverable. During the generation of the data deliverable, the workstation 125 may provide tracking information, such as checkpoint tracking and project documentation, to the project tracking computers 110. In this regard, the project may be tracked and subsequent audits may be performed. Additionally, once a project has been completed, a data deliverable may be transmitted or communicated to any number of suitable data recipients 130, such as various healthcare providers that are customers of the service provider. Alternatively, the workstation 125 may direct the transmission of a data deliverable to a data recipient 130.

Additionally, as desired, any number of data recipients 130 may be provided. Each data recipient 130 may be a suitable processor-driven device configured to receive information associated with data delivery projects. As such, a data recipient 130 may include components similar to those described above for the project tracking computers 110 and/or the project review computers 115. For example, a data recipient 130 may include any number of processors, memory devices, I/O interfaces, and/or network interfaces. In operation, a data recipient 130 may be configured to receive a data deliverable prepared in conjunction with a project. For example, a data deliverable may be received from a workstation 125 or from another service provider system that accesses, maintains, and/or manages healthcare information. In certain embodiments, a data deliverable may be a one time deliverable, such as the results of an ad-hoc query. In other embodiments, a data deliverable may be a data feed that is received in a recurring manner.

With continued reference to FIG. 1, any number of auditor devices 135 may be provided. Each auditor device 135 may be a suitable processor-driven device that facilitates the auditing of a project. As such, an auditor device 135 may include components similar to those described above for the project tracking computers 110 and/or the project review computers 115. For example, an auditor device 135 may include any number of processors, memory devices, I/O interfaces, and/or network interfaces. In operation, an auditor may utilize an auditor device 135 to identify a project to be audited and/or to receive an indication of a project to be audited. Additionally, the auditor device 135 may be utilized to access and/or receive project tracking information associated with the project. During the completion of an audit, the auditor device 135 may facilitate the entry and/or receipt of audit results. For example, an auditor may determine whether various checkpoints associated with the project control process have been followed, and the auditor may enter appropriate audit result information into an audit form. Once an audit has been performed and/or during the completion of an audit, the audit results may be provided by the auditor device 135 to the project review computers 115 for additional analysis.

Once an audit has been completed and/or a process adoption score has been calculated, one or more messages associated with the audit and/or process adoption score may be generated and communicated to one or more recipient devices 140. Each recipient device 140 may be a suitable processor-driven device that facilitates the receipt of audit results and/or messages generated in association with an audit analysis. As such, a recipient device 140 may include components similar to those described above for the project tracking computers 110 and/or the project review computers 115. For example, a recipient device 140 may include any number of processors, memory devices, I/O interfaces, and/or network interfaces. Examples of suitable recipient devices include, but are not limited to, personal computers, portable devices, mobile devices, and the like. In operation, a recipient device 140 may be configured to receive any number of results associated with an audit, such as a process adoption score and/or information associated with exceptions generated during an audit. Additionally, the recipient device 140 may be configured to receive any number of alert messages generated by the project review computers 115, such as alert messages associated with relatively low process adoption scores, alert messages associated with identified exceptions, and/or alert messages associated with abnormal project development behavior.

The networks 120 may include any number of telecommunication and/or data networks, whether public, private, or a combination thereof, including a local area network, a public switched telephone network, a wide area network, an intranet, the Internet, intermediate handheld data transfer devices, and/or any combination thereof and may be wired and/or wireless. For example, the networks 120 may include a public switched telephone network that facilitates telephone communication between various devices within the system 100.

Due to network connectivity, various methodologies as described herein may be practiced in the context of distributed computing environments. Although certain components of the system 100 are shown for simplicity as being in communication with one another via one intervening network 120, it is to be understood that any other network configuration is possible. For example, intervening network 120 may include a plurality of networks, each with devices such as gateways and routers for providing connectivity between or among networks 120. Instead of or in addition to a network 120, dedicated communication links may be used to connect the various devices in accordance with an example embodiment of the invention.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one embodiment, the computing system 105 (or other computer) may be implemented as a specialized processing machine that includes hardware and/or software for performing the methods described herein. Accordingly, embodiments of the invention should not be construed as being limited to any particular operating environment, system architecture, or device configuration.

Figure 2:
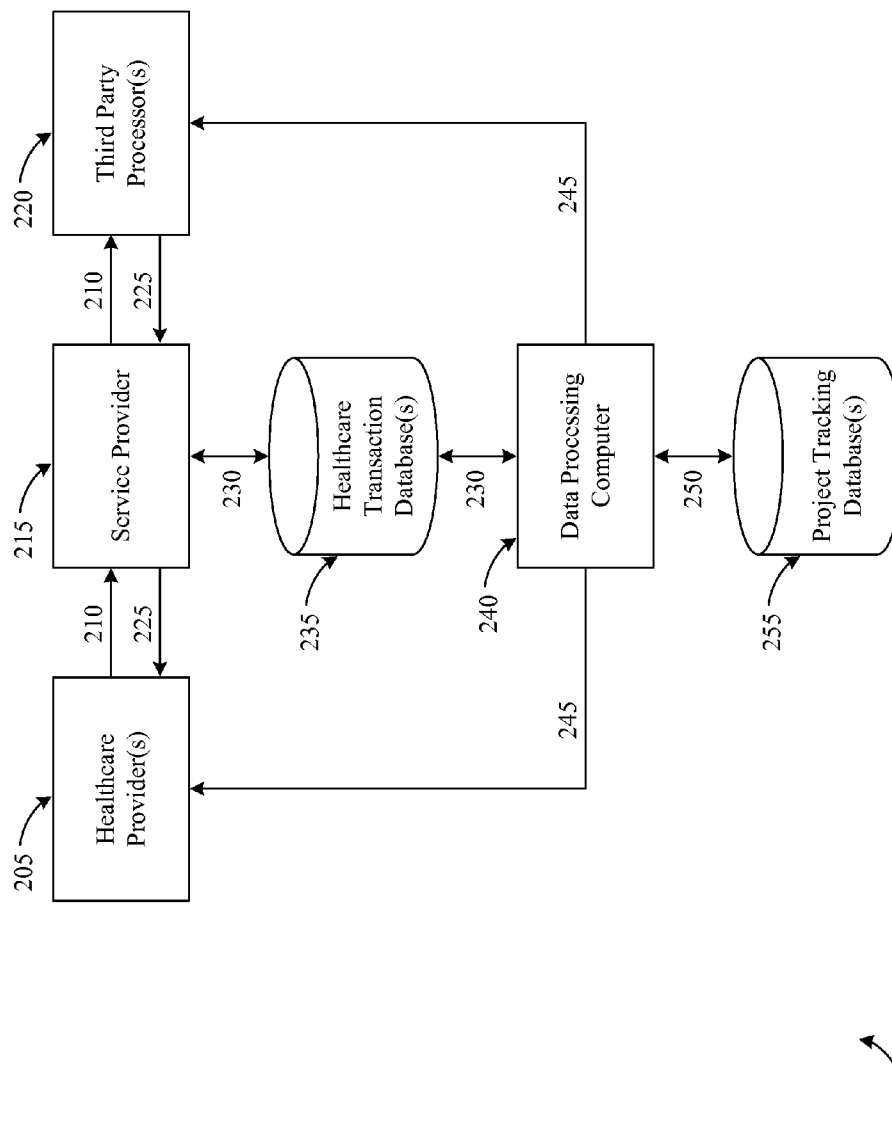
FIG. 2 illustrates a block diagram of an example system that may be utilized to generate or prepare projects relating to healthcare information, according to illustrative embodiments of the invention.

Embodiments of the invention may be utilized in conjunction with a wide variety of different applications and projects. Indeed, embodiments of the invention may be applicable to any project in which a project control process is instituted in order to develop a software product or a data deliverable. For example, embodiments of the invention may be applicable to the evaluation of projects directed to the delivery of confidential healthcare information. In this regard, determinations may be made as to whether the projects adhere to suitable project control processes. FIG. 2 illustrates a block diagram of an example system 200 that may be utilized to collect healthcare information and generate or prepare projects relating to the collected healthcare information.

With reference to FIG. 2, healthcare providers 205, such as pharmacies, hospitals, and/or physician's offices, may generate healthcare transactions 210 (e.g., prescription claim transactions, eligibility transactions, electronic prescriptions, etc.), and the healthcare transactions 210 may be communicated to a service provider 215. In certain embodiments, the service provider 215 may be a switch/router that routes healthcare transactions and/or other healthcare requests. For example, the service provider 215 may be configured to route billing requests and/or prescription claim requests communicated from the healthcare providers 205 to designated third party processors 220, such as claims processors (e.g., pharmacy benefits managers ("PBMs"), insurers, Medicare payers, government payers, claims clearinghouses, etc.) and/or other healthcare providers.

Once a healthcare transaction 210 has been routed to a third party processor 220, the healthcare transaction 210 may be processed and/or adjudicated by the third party processor 220. For example, the third party processor 220 may determine benefits coverage associated with a healthcare claim transaction. As another example, the third party processor 220 may determine patient healthcare coverage eligibility. Once the healthcare transaction 210 has been processed or adjudicated, the third party processor 220 may return a response 225 for the healthcare transaction 210 to the service provider 215. The response 225 may be processed by the service provider 215 and routed to the healthcare provider 205.

During the processing of healthcare transactions 210 and/or adjudicated responses 225, the service provider 215 may perform a wide variety of edits and/or other analysis. For example, the service provider 215 may verify data included in transactions 210 or responses 225 and/or the formatting of the transactions 210 or responses 225. Additionally, the service provider 215 may store information 230 associated with the healthcare transactions 210 and/or responses 225 in any number of suitable memory devices, such as one or more healthcare transaction databases 235.

As desired, at least a portion of the stored healthcare transaction information 230 may be accessed during the preparation of a data delivery project. For example, a technician may utilize a data processing computer 240, such as one of the workstations 125 illustrated in FIG. 1, to obtain a portion of the stored healthcare transaction information 230. The stored healthcare transaction information 230 may then be utilized in the completion of a data delivery project. In other words, the stored healthcare transaction information 230 may be utilized to prepare a data deliverable 245, such as an ad-hoc query or a data feed. Once prepared, the data deliverable 245 may be provided to one or more recipients, such as a healthcare provider 205 or a third party processor 220.

Additionally, during the preparation of the data delivery project and/or following the completion of the data delivery project, tracking information 250 associated with the project may be stored in one or more project tracking databases 255. For example, project documentation, notes, and/or critical date information for the project may be stored. In certain embodiments, an issue-tracking application, such as an open source issue-tracking Web application (e.g., JTrac, etc.), may be utilized to collect and store the project tracking information. As a result of storing project tracking information, subsequent audits may be performed in order to determine whether the project was developed in accordance with a project control process. In this regard, adherence to the project control process and/or adoption of the project control process may be evaluated.

A wide variety of various project control processes may be utilized as desired in various embodiments of the invention. A project control process may establish checkpoints and/or parameters that control and/or govern the development of a project, such as a data delivery project. In certain embodiments, the project control process may be instituted in order to enhance the security of sensitive information, such as confidential healthcare information. One example project control process 300 will now be described with respect to FIG. 3.

Figure 3:
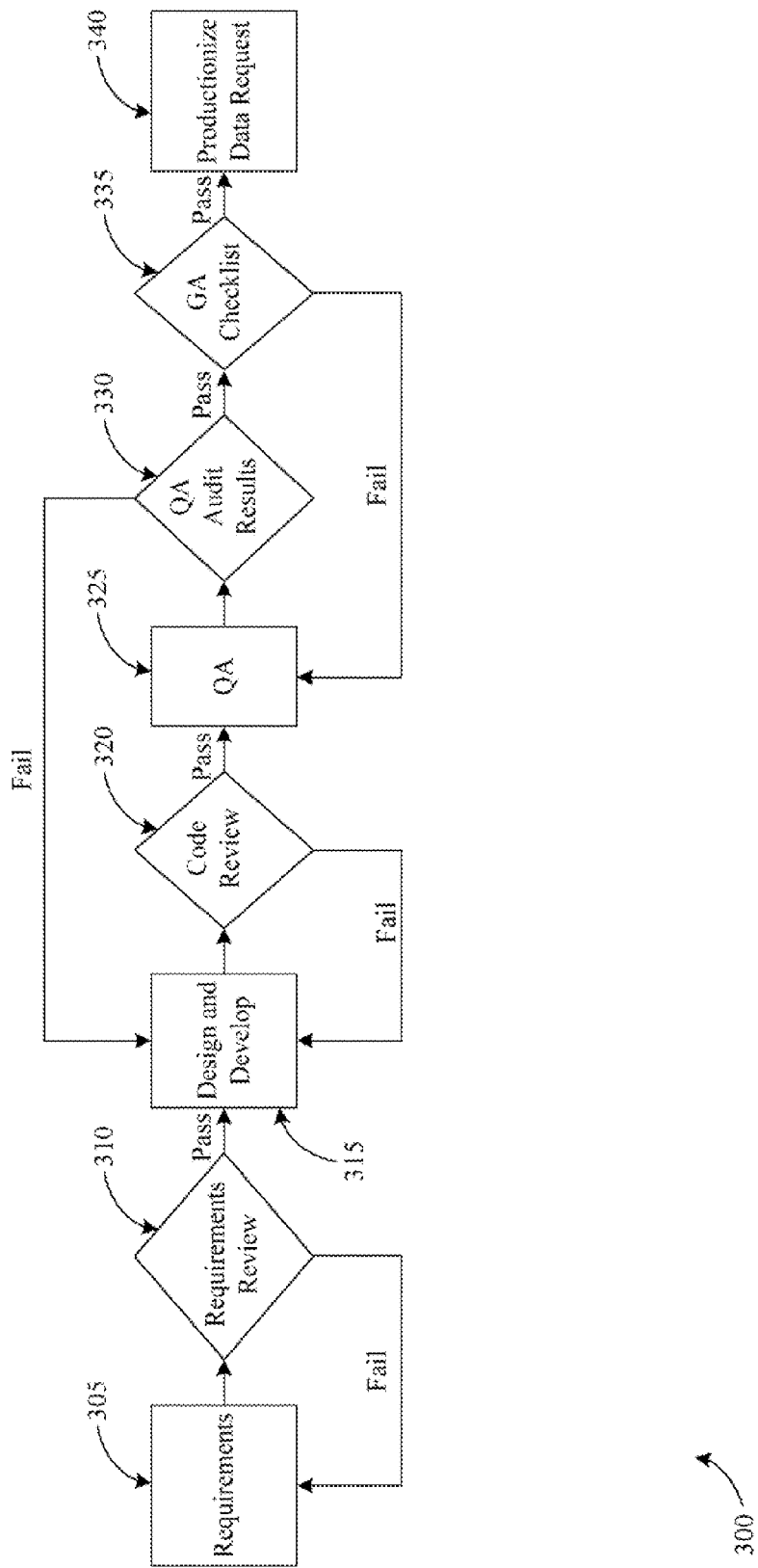
FIG. 3 is a block diagram of an example project control process for preparing data delivery projects, according to an illustrative embodiment of the invention.

Turning to FIG. 3, an example project control process 300 may include a plurality of checkpoints intended to mitigate risk and exposure relating to the delivery of proprietary and/or confidential healthcare information. For example, as shown, the process 300 may include eight process steps; however, any number of steps or checkpoints may be utilized as desired in various embodiments of the invention.

First, the requirements 305 for a data delivery project may be identified and/or defined. For example, a customer request for data may be evaluated in order to identify the requirements for a data delivery project. In certain embodiments, a data request form may be received, evaluated, and/or completed in order to identify the requirements for the data delivery project. As desired, the data request form and/or other requirements information may be stored in a project tracking database. Following the identification of project requirements, a project requirements review meeting 310 may be held in order to evaluate the project requirements, manage the project requirements, and/or evaluate cross-functional communication. In the event that the project fails to pass at the requirements review stage 310, then the project development process 300 may return to the requirements stage 305. Otherwise, the project development process 300 may continue at the design and development stage 315.

At the design and development stage 315, the data delivery project may be coded and/or otherwise developed. In other words, suitable code and/or commands for accessing or obtaining the data to be included in a data deliverable may be developed. A code review meeting 320 or other peer review of the code may then be completed. In the event that the code fails to pass the code review stage 320, then the project development process 300 may continue at the design and development stage 315. Otherwise, the project development process 300 may continue at a quality control and analysis ("QA") stage 325. At the QA stage 325, a wide variety of different quality control tests and/or operations may be performed on the data delivery project. In other words, a quality control audit may be performed. The results of the quality control audit may then be evaluated at a QA audit stage 330. In the event that the project fails to pass the QA audit stage 330, then the project development process 300 may return to the design and development stage 315. Otherwise, the project development process 300 may continue at a generally available ("GA") stage 335.

At the GA stage 335, a GA quality and process control checklist may be completed for the project in order to determine whether the data may be delivered to a customer. In the event that the GA stage 335 is not passed, then the project development process 300 may return to the QA stage 325. Otherwise, the project development process 300 may continue at a production stage 340, and the data may be delivered to a customer.

At each step of the process 300, a wide variety of information associated with the data delivery project may be tracked. Additionally, tracking information may be stored in one or more suitable project tracking databases. A wide variety of different information may be tracked as desired in various embodiments of the invention, including but not limited to, project documentation, notes, checklists, and/or date information. As a result of maintaining tracking information, a subsequent audit may be performed in order to evaluate adherence of the project development to the project control process 300.

Operational Overview

As described herein, audits may be performed on data delivery projects in order to evaluate adherence to one or more project control processes. FIG. 4 is a flow diagram of an example method 400 for evaluating a data delivery project for adherence to a project control process, according to an illustrative embodiment of the invention. The method 400 may be performed by a suitable project review computer and/or review module, such as the project review computer 115 and/or review module 184 illustrated in FIG. 1. The method 400 may begin at block 405.

At block 405, a project may be identified for an audit. A wide variety of suitable methods and or techniques may be utilized as desired to identify a project for audit. For example, a project may be identified based at least in part upon the receipt of a project selection from an auditor. As another example, tracking information for completed projects may be evaluated utilizing one or more suitable identification parameters, and a project may be selected for an audit based at least in part upon the evaluation. For example, a project having unexpected dates for one or more benchmarks and/or any number of other identifiable criteria that do not satisfy expected values may be identified. Additionally, in certain embodiments, one or more projects may be periodically identified for audit purposes. For example, a fixed number of projects may be identified in a month. In other embodiments, projects may be automatically audited following completion. One example of the operations that may be performed at block 405 is described in greater detail below with reference to FIG. 5.

At block 410, an audit may be performed on the project, and the results of the audit may be identified. The audit may evaluate adherence of the project to a project control process. In other words, the audit may evaluate whether the project control process has been properly utilized during the development of the project. In this regard, a determination may be made as to whether the process is being adopted and/or followed. A wide variety of suitable methods and/or techniques may be utilized as desired to identify the results of an audit. In certain embodiments, one or more audit forms may be provided to an auditor along with project tracking information, and the auditor may perform a manual audit of the project. The results of the manual audit may then be returned to a suitable computing system that identifies and further processes the results. In other embodiments, an audit may be performed in an automated fashion. For example, one or more audit parameters and/or checkpoints may be identified, and project tracking information may be evaluated utilizing the parameters and/or checkpoints. In other embodiments, certain audit operations may be performed manually while other audit steps are performed in an automated fashion.

In certain embodiments, an audit may determine whether various steps or checkpoints associated with a project control process have been adhered to and/or followed. Additionally, as desired, an audit may determine whether the completion of various steps of the process has been properly documented. In certain embodiments, an audit may be an objective audit in which respective values are assigned to each of the checkpoints and/or documentation parameters. As desired, the respective values assigned to each of the checkpoints and/or parameters may be weighted based upon the respective importance of the checkpoints (e.g., the security risk if the checkpoint is not completed or followed, etc.). Once the audit results have been determined, the results may be evaluated at block 415 in order to calculate a process adoption score for the project. For example, the respective values for each of the checkpoints may be summed together in order to calculate a process adoption score. The process adoption score may be indicative of the adherence of the project development or generation to the project control process. Additionally, the results may be evaluated in order to determine whether any exceptions are present (e.g., an exception associated with a checkpoint not being achieved, etc.). One example of the operations that may be performed at blocks 410 and 415 is described in greater detail below with reference to FIG. 6.

At block 420, any number of communications associated with an audit, a process adoption score, and/or identified exceptions may be generated and communicated to any number of desired recipient devices, such as the recipient devices 140 illustrated in FIG. 1. For example, a process adoption score may be communicated to a technician who performed an audit and/or to a supervisor of the technician. As another example, alert messages associated with audit exceptions and/or relatively low process adoption scores may be communicated to a supervisor of a technician who completed the project. In this regard, corrective action may be taken to promote adoption of the project control process.

The method 400 may end following block 420.

Figure 4:
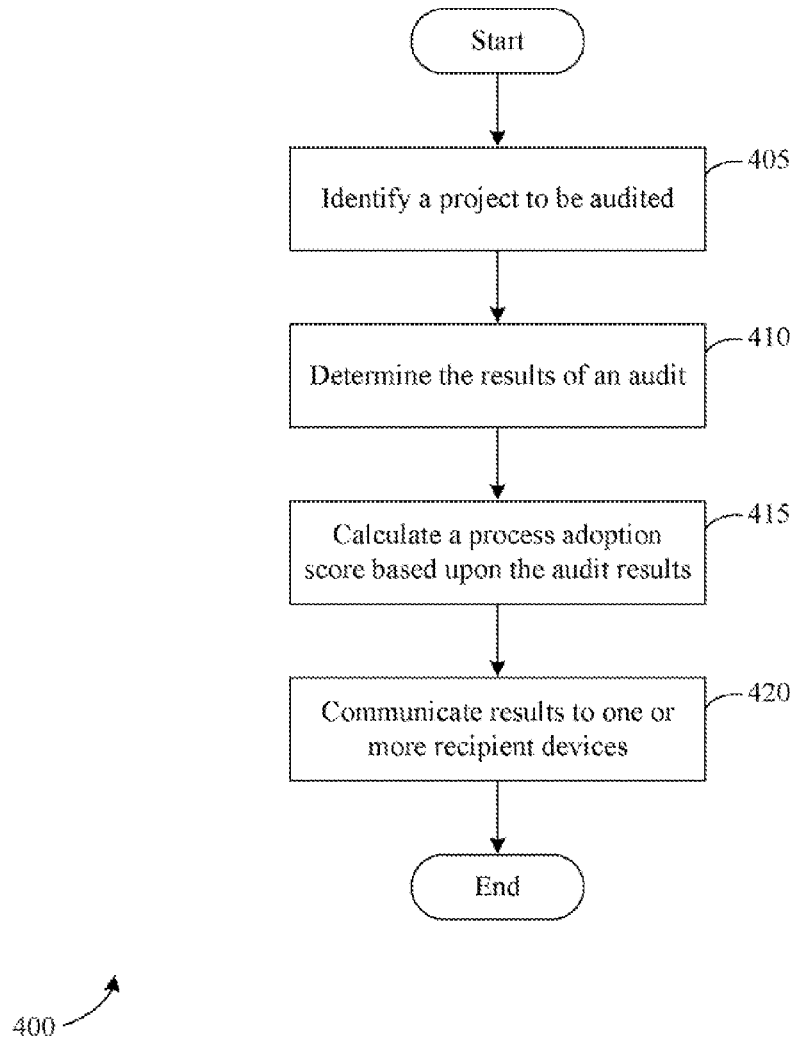
FIG. 4 is a flow diagram of an example method for evaluating a data delivery project for adherence to a project control process, according to an illustrative embodiment of the invention.
Figure 5:
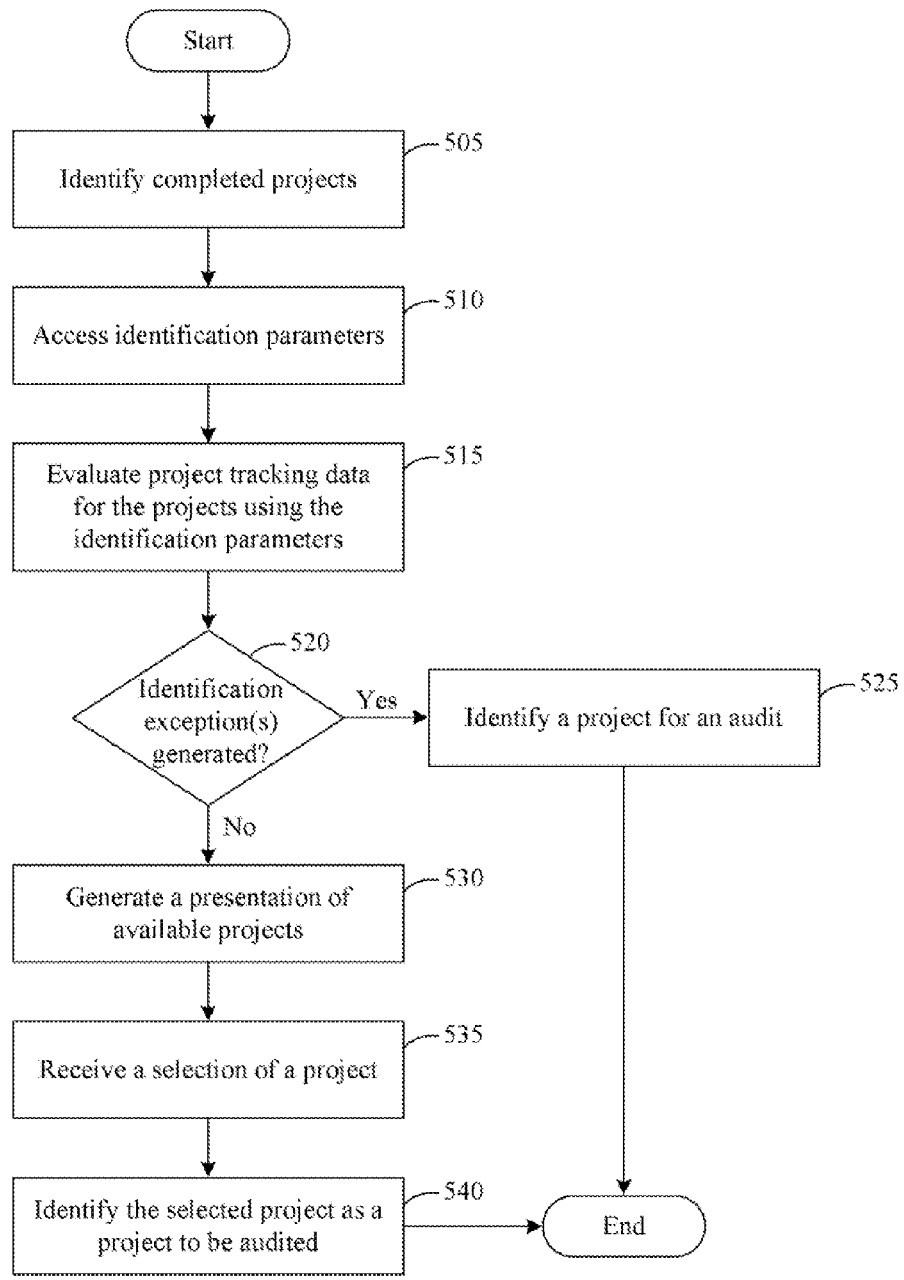
FIG. 5 is a flow diagram of an example method for identifying a data delivery project to be audited, according to an illustrative embodiment of the invention.

FIG. 5 is a flow diagram of an example method 500 for identifying a data delivery project to be audited, according to an illustrative embodiment of the invention. The method 500 illustrated in FIG. 5 may be an example implementation of block 405 shown in FIG. 4. As such, the method 500 may be performed by a suitable project review computer and/or review module, such as the project review computer 115 and/or review module 184 illustrated in FIG. 1. The method 500 may begin at block 505.

At block 505, one or more completed projects may be identified. For example, project tracking information may be accessed and analyzed in order to identify projects that have been marked as complete. At block 510, which may be optional in certain embodiments of the invention, one or more identification parameters may be accessed and/or determined. The identification parameters may include suitable parameters associated with the identification of projects to be audited, including but not limited to, expected date parameters, parameters associated with whether project documentation has been completed, parameters utilized to evaluate project documentation, parameters associated with the delivered content, parameters associated with a recipient of the delivered content, and/or parameters associated with the completion of project tracking requirements.

At block 515, project tracking data associated with the completed projects may be evaluated utilizing the accessed one or more identification parameters. In this regard, a respective determination may be made as to whether one or more of the completed projects should be audited. For example, a determination may be made at block 520 as to whether one or more exceptions are triggered based upon the evaluation of the project tracking data with the identification parameters. As one example, a determination may be made as to whether an unexpected date is included in the project tracking data for a project. As another example, a determination may be made as to whether expected tracking data for a project is missing. If it is determined at block 520 that an identification exception has been triggered for a project, then operations may continue at block 525, and the project may be identified as a project to be audited. Operations may then end following block 525.

If, however, it is determined at block 520 that no identification exceptions have been generated, then operations may continue at block 530. At block 530, identification information for at least a portion of the completed projects may be utilized to generate a presentation of projects available for an audit. The generated presentation may then be provided to an auditor. For example, a list of available projects may be generated, and the list may be communicated to an auditor device for presentation to the auditor. A wide variety of suitable communications techniques and/or formats may be utilized to provide the generated list to the auditor, such as email and/or one or more Web pages. Additionally, in certain embodiments, the available projects may be randomized prior to presentation to the auditor. Following the provision of a presentation to an auditor, an auditor selection of a project may be received at block 535. Based upon the received selection, the selected project may be identified at block 540 as a project to be audited. Operations may then end following block 540.

The method 500 may end following either block 525 or block 540.

Figure 6:
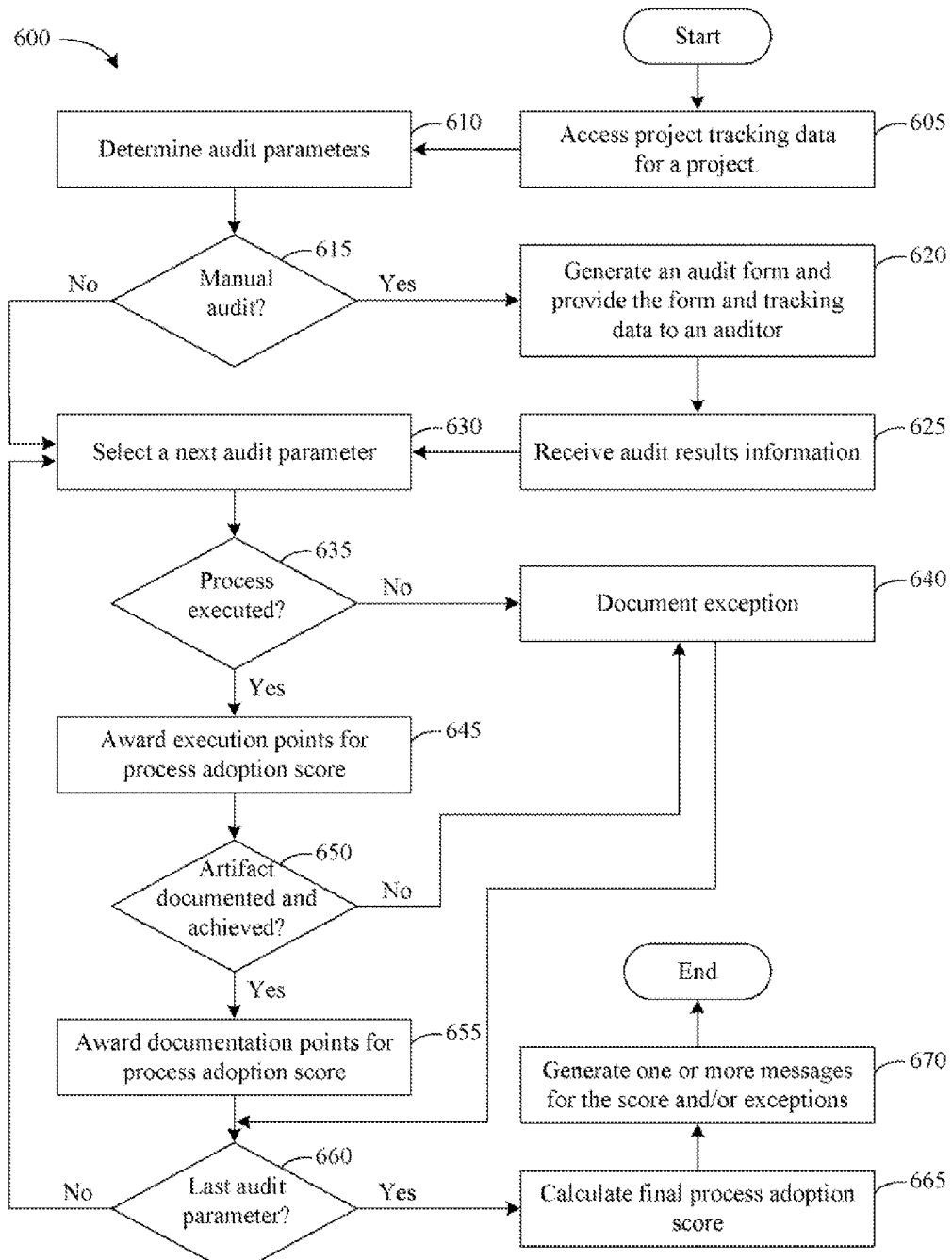
FIG. 6 is a flow diagram of an example method for determining the results of an audit performed on a data delivery project, according to an illustrative embodiment of the invention.

FIG. 6 is a flow diagram of an example method 600 for determining the results of an audit performed on a data delivery project, according to an illustrative embodiment of the invention. The method 600 illustrated in FIG. 6 may be an example implementation of blocks 410 and 415 shown in FIG. 4. As such, the method 600 may be performed by a suitable project review computer and/or review module, such as the project review computer 115 and/or the review module 184 illustrated in FIG. 1. The method 600 may begin at block 605.

At block 605, project tracking data for a project may be accessed in association with an audit to be performed on the project. For example, project tracking information previously stored during the development of the project may be accessed from one or more suitable project tracking databases. At block 610, one or more audit parameters may be identified and/or determined. The audit parameters may establish a wide variety of conditions and/or checkpoints to be evaluated during the completion of the audit. In certain embodiments, the audit parameters may be defined by and/or based upon a project control process that was established to control project development. Examples of suitable audit parameters include, but are not limited to, client specification parameters, data request form parameters, review meeting parameters, code review parameters, quality control parameters, data feed evaluation parameters, generally available parameters, documentation parameters, and/or date parameters.

At block 615, a determination may be made as to whether a manual audit will be performed on the project. In other words, a determination may be made as to whether project tracking information will be provided to an auditor to facilitate the completion of an audit. If it is determined at block 615 that a manual audit will not be performed, then an automated audit may be performed, and operations may continue at block 630 described in greater detail below. If, however, it is determined at block 615 that a manual audit will be performed, then operations may continue at block 620.

At block 620, one or more audit forms may be accessed and/or generated. An audit form may include parameters and/or checkpoints to be evaluated by an auditor during the completion of an audit. In certain embodiments, the audit form may be an electronic form that additionally includes data entry fields that facilitate the receipt of audit results. Once the audit form(s) have been accessed and/or generated, the audit form(s) may be provided to an auditor device, such as an auditor device 135 illustrated in FIG. 1. Additionally, in certain embodiments, project tracking information may be provided to the auditor device 135. For example, project tracking information may be provided via one or more suitable Web pages or other network communication displays. An auditor may evaluate the project tracking information and complete an audit for the project. In certain embodiments, the auditor may enter audit results into the audit form(s). For example, an auditor may enter indications associated with whether various checkpoints and/or stages of the project development process have been completed and/or adequately documented. Following completion of the manual audit, audit results information may be returned by the auditor device 135, and the audit results information may be received at block 625. Operations may then continue at block 630.

At block 630, a next audit parameter may be selected for evaluation. In the event of a manual audit, the audit parameter may be selected in order to facilitate the analysis of received audit results information. In the event of an automated or partially automated audit, the audit parameter may be selected to facilitate the evaluation of project tracking information associated with the audited project. For purposes of further description, the audit parameter is described as a parameter associated with a stage or checkpoint to be completed during the development of a project. For example, the audit parameter may be a stage or checkpoint of a project development process. However, it will be appreciated that any number of audit parameters may be associated with a stage of the project development process. For example, a plurality of parameters may be utilized in an automated audit in order to determine whether a process stage has been adequately completed and/or documented.

At block 635, a determination may be made as to whether the process stage associated with the selected audit parameter has been completed and/or executed. In other words, a determination may be made as to whether a technician assigned to the process stage completed the process stage. If it is determined at block 635 that the process stage has been not been completed or executed, then operations may continue at block 640. At block 640, an exception may be generated and/or flagged for the process stage. Additionally, a determination may be made that process adoption points will not be awarded for the process stage. Alternatively, process adoption points may be subtracted for the process stage. In either case, a process adoption score for the project may be reduced or lowered. Operations may then continue at block 660.

If, however, it is determined at block 635 that the process stage has been completed or executed, then operations may continue at block 645. At block 645, execution points may be awarded for the process stage. In other words, an indicator of process adoption may be increased based upon a determination that the process stage has been adhered to and/or completed. In certain embodiments of the invention, the number of points awarded for the process stage may be predetermined. In other words, if the stage has been completed, then a predetermined number of points associated with the process stage may be awarded. As desired, the number of points associated with a particular process stage may be weighted relative to other stages of the process. For example, the criticality of a process stage may be taken into consideration when determining the points associated with the process stage. In this regard, a greater number of points may be assigned to stages that are more likely to lead to a security breach or unintended disclosure of confidential information. Following block 645, operations may continue at block 650.

At block 650, a determination may be made as to whether the process stage or artifact has been adequately documented. In other words, a determination may be made as to whether the technician documented work performed for the process stage. As part of this determination, a determination may be made as to whether the process stage was marked or documented as completed. If it is determined at block 650 that the process stage has not been adequately documented, then operations may continue at block 640, and an exception may be generated and/or flagged for the documentation of the process stage. Additionally, a determination may be made that process adoption points will not be awarded for the process stage documentation. Alternatively, process adoption points may be subtracted for the failed documentation of the process stage. In either case, a process adoption score for the project may be reduced or lowered. Operations may then continue at block 660.

If, however, it is determined at block 650 that the process stage has been adequately documented, then operations may continue at block 655. At block 655, documentation points may be awarded for the process stage. In other words, an indicator of process adoption may be increased based upon a determination that the process stage has been adequately documented. In certain embodiments of the invention, the number of points awarded for the process stage may be predetermined. In other words, if the stage has been documented, then a predetermined number of points associated with the process stage documentation may be awarded. As desired, the number of points awarded may be weighted relative to other components of the process. For example, the criticality of a documentation may be taken into consideration when determining the points associated with the process stage. Following block 655 operations may continue at block 660.

At block 660, a determination may be made as to whether the last audit parameter or checkpoint has been reached and/or evaluated. If it is determined at block 660 that the last audit parameter has not been reached, then operations may continue at block 630, and a next audit parameter may be selected for evaluation. If, however, it is determined at block 660 that the last audit parameter has been reached and/or evaluated, then operations may continue at block 665. At block 665, a final process adoption score may be calculated or determined for the project. For example, the respective values for each of the audit parameters and/or process stages may be combined in order to calculate a final process adoption score. As another example, a total number of points to be subtracted may be determined, and a final process adoption score may be calculated. The final process adoption score may be indicative of the adherence of the project development to the project control process. In other words, the final process adoption score may reflect adoption and/or proper use of the project control process.

At block 670, which may be optional in certain embodiments of the invention, one or more messages associated with the audit may be generated. A wide variety of different types of messages may be generated and/or prepared as desired in various embodiments of the invention. Examples of suitable messages include, but are not limited to, a message that includes a calculated process adoption score, an alert message generated as a result of a relatively low process adoption score, an alert message associated with an exception triggered by an audit (e.g., a failed process stage or checkpoint, a failure to document a process stage, etc.), and/or an error message associated with process development exception (e.g., excessive coding and/or code review exceptions, exceptions associated with required redelivery of data, etc.). Messages may be generated or prepared for communication to a wide variety of different recipients, such as a technician that prepared the project and/or a supervisor of the technician. Additionally, as desired, information associated with the audit, process adoption score, and/or identified exceptions may be stored for subsequent access.

The method 600 may end following block 670.

The operations described and shown in the methods 400, 500, and 600 of FIGS. 4-6 may be carried out or performed in any suitable order as desired in various embodiments of the invention. Additionally, in certain embodiments, at least a portion of the operations may be carried out in parallel. Furthermore, in certain embodiments, less than or more than the operations described in FIGS. 4-6 may be performed.

Figure 7:
FIG. 7 illustrates an example form that may be completed during a project audit, according to an illustrative embodiment of the invention.

In certain embodiments of the invention, such as embodiments in which an audit is manually performed, a wide variety of different types of audit forms may be generated, accessed, and/or provided to auditors. For example, an audit form may be provided to an auditor in conjunction with project tracking information to facilitate the completion of an audit. FIG. 7 illustrates an example form 700 that may be completed during a project audit, according to an illustrative embodiment of the invention.

The form 700 may include a wide variety of information, such as project identification information 705, technician, date, and/or review information 710, checkpoint and/or process stage audit information 715, and/or special exception information 720. The project identification information 705 may include any number of data fields that identify a data delivery project, such as a project number, a project summary, and/or a project description. The technician, date, and/or review information 710 may include any number of data fields, such as a project origination date, a GA date, a developer name, an identifier of a code review, an identifier of a quality control analyst, and/or an identifier of an individual who signed off at the GA stage.

With continued reference to the form 700, the process stage audit information 715 may include identifiers for a wide variety of different process stages or checkpoints and/or identifiers for a wide variety of different documentation stages. Additionally, the process stage audit information 715 may include respective process adoption score point values that are assigned to each stage. As desired, the various point values may be weighted. For example, the values may be weighted based at least in part upon the criticality of the various stages and/or the potential risks in the event that the stages are not satisfied. According to an aspect of the invention, data entry fields may be included in the form in order to permit an auditor to enter indications associated with the completion of each stage. In this regard, the point values for the audit may be determined, and a process adoption score may be calculated.

The special exception information 720 may include any number of fields associated with special conditions that may be identified during an audit. For example, if a project required a redelivery of data due to an initial missed process stage, then an entry may be made to facilitate reduction of a process adoption score. As another example, if the project required an unusual number of iterations for a process stage, such as an unusually high number of code review iterations (e.g., more than two code review iterations), then an entry may be made to facilitate reduction of the process adoption score and/or the triggering of an exception.

In certain embodiments, at least a portion of the fields included in the form 700 may be finable. In other words, certain fields may be configured to accept data entry from a technician who is completing an audit. Other fields, such as the project identification information 705 and/or the technician, date, and/or review information 710, may be prefilled based upon stored project tracking information. The fields and/or information illustrated in the form 700 of FIG. 7 are provided by way of example only. As desired, a wide variety of other information and/or combinations of fields may be included in an audit form in accordance with embodiments of the invention.

Example embodiments of the invention can provide the technical effects of evaluating data delivery projects in order to access and/or determine adherence of the data delivery projects to a project control process. In this regard, adoption and/or adherence to the project control process may be determined and/or evaluated. As desired, various alerts and/or corrective actions may be taken based upon the evaluation in order to encourage adoption of the project control process. As a result, security associated with confidential and/or propriety data that is included in the data delivery projects may be enhanced.

Various block and/or flow diagrams of systems, methods, apparatus, and/or computer program products according to example embodiments of the invention are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer-usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method, comprising:
   identifying, by a computing system comprising one or more computers, a project to be audited, the project comprising a data delivery project implemented to deliver data comprising confidential healthcare information and project tracking information comprising information regarding actions performed during development of the data delivery project;
   identifying, by the computing system, one or more audit parameters;
   evaluating, by the computing system utilizing the one or more audit parameters, the project tracking information associated with the project;
   determining, by the computing system, based at least in part upon the evaluation, the results of the audit wherein the audit evaluates adherence of the project to a project control process and wherein determining the results of the audit comprises:
   determining, by the computing system, for each of a plurality of checkpoints in the project control process for the development of the project if the checkpoint has been followed;
   assigning, by the computing system, a first score based on the checkpoint followed determination;
   determining, by the computing system, for each of the plurality of checkpoints whether completion of the checkpoint was properly documented;
   assigning, by the computing system, a second score based on the documentation determination; and
   calculating, by the computing system based at least in part upon the results of the audit, a process adoption score for the identified project, wherein the process adoption score comprises the sum of the first score and the second score for each of the plurality of checkpoints in the project control process for the development of the project.

2. The computer-implemented method of claim 1, wherein identifying a project to be audited comprises identifying a project based upon the receipt of a project selection from an auditor.

3. The computer-implemented method of claim 1, wherein identifying a project to be audited comprises:
   evaluating, by the computing system, tracking information associated with at least one completed project; and
   identifying, by the computing system based at least in part upon the evaluation, the project to be audited.

4. The computer-implemented method of claim 1, wherein determining the results of an audit comprises:
   providing, by the computing system to a device associated with an auditor, an audit form; and
   receiving, by the computing system, audit results input into the audit form by the auditor.

5. The computer-implemented method of claim 4, further comprising:
   providing, by the computing system to the device associated with the auditor, tracking information associated with the project.

6. The computer-implemented method of claim 1, wherein determining the results of an audit comprises determining respective values for a plurality of audit parameters associated with adherence to the project control process and wherein calculating a process adoption score comprises calculating a process adoption score based at least in part upon the respective values.

7. The computer-implemented method of claim 1, further comprising:
   identifying, by the computing system based at least in part upon the determined results of the audit, one or more exceptions associated with the adherence of the project to the project control process.

8. The computer-implemented method of claim 1, further comprising:
   generating, by the computing system based at least in part upon the calculated process adoption score, an alert message associated with the project; and
   communicating, by the computing system to a recipient device, the generated alert message.

9. The computer-implemented method of claim 1, wherein project tracking information comprises at least one of checkpoint tracking information; project documentation, project notes, and critical date information for the development of the project.

10. A system, comprising:
    at least one memory operable to store computer-executable instructions; and at least one processor configured to access the at least one memory and execute the computer-executable instructions to:
  identify a project to be audited, the project comprising a data delivery project implemented to deliver data comprising confidential healthcare information and project tracking information comprising information regarding actions performed during development of the data delivery project;
  identify one or more audit parameters;
  evaluate, utilizing the one or more audit parameters, the project tracking information associated with the project;
  determine, based at least in part upon the evaluation, the results of the audit performed on the identified project, wherein the audit evaluates adherence of the project to a project control process and wherein the at least one processor is configured to determine the results of the audit by executing the computer-executable instructions to:
    determine, for each of a plurality of checkpoints in the project control process for the development of the project, if the checkpoint has been followed;
    assign a first score based on the checkpoint followed determination;
    determine, for each of the plurality of checkpoints, whether completion of the checkpoint was properly documented; and
    assign a second score based on the documentation determination; and
  calculate, based at least in part upon the results of the audit, a process adoption score for the identified project, wherein the process adoption score comprises the sum of the first score and the second score for each of the plurality of checkpoints in the project control process for the development of the project.

11. The system of claim 10, wherein the project to be audited is identified based upon the receipt of a project selection from an auditor.

12. The system of claim 10, wherein the at least one processor is configured to identify the project to be audited by executing the computer-executable instructions to:
  evaluate tracking information associated with at least one completed project; and
  identify the project to be audited based at least in part upon the evaluation.

13. The system of claim 10, wherein the at least one processor is configured to determine the results of the audit by executing the computer-executable instructions to:
  provide, by the computing system to a device associated with an auditor, an audit form; and
  receive audit results input into the audit form by the auditor.

14. The system of claim 13, wherein the at least one processor is further configured to execute the computer-executable instructions to:
  provide, to the device associated with the auditor, tracking information associated with the project.

15. The system of claim 10, wherein the results of an audit comprise respective values for a plurality of audit parameters associated with adherence to the project control process and wherein the process adoption score comprises a process adoption score based at least in part upon the results of the audit.

16. The system of claim 10, wherein the at least one processor is configured to determine the results of the audit by executing the computer-executable instructions to:
  identify, based at least in part upon the determined results of the audit, one or more exceptions associated with the adherence of the project to the project control process.

17. The system of claim 10, wherein the at least one processor is configured to determine the results of the audit by executing the computer-executable instructions to:
  generate, based at least in part upon the calculated process adoption score, an alert message associated with the project; and
  direct communication of the generated alert message to a recipient device.

18. The system of claim 10, wherein project tracking information comprises at least one of: checkpoint tracking information, project documentation, project notes, and critical date information for the development of the project.

* * * * *